United States Patent
Fischell et al.

(10) Patent No.: US 6,272,379 B1
(45) Date of Patent: *Aug. 7, 2001

(54) IMPLANTABLE ELECTRONIC SYSTEM WITH ACUTE MYOCARDIAL INFARCTION DETECTION AND PATIENT WARNING CAPABILITIES

(75) Inventors: Robert E. Fischell, Dayton, MD (US); David R. Fischell, Fair Haven, NJ (US); Tim A. Fischell, Richland, MI (US)

(73) Assignee: Cathco, Inc., Dayton, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/271,219

(22) Filed: Mar. 17, 1999

(51) Int. Cl.[7] .............................. A61N 1/39; A61B 5/0452
(52) U.S. Cl. ..................................... 607/5; 607/9; 607/63; 600/517; 600/515
(58) Field of Search ..................................... 600/509, 515, 600/517, 523; 607/2, 3, 4, 5, 9, 25, 30, 32, 60, 62

(56) References Cited

U.S. PATENT DOCUMENTS

| | | | |
|---|---|---|---|
| 3,867,950 | 2/1975 | Fischell | 128/419 P |
| 3,888,260 | 6/1975 | Fischell | 128/419 P |
| 4,003,379 | 1/1977 | Ellinwood | 128/260 |
| 4,223,678 | 9/1980 | Langer et al. | 128/419 D |
| 4,295,474 | 10/1981 | Fischell | 128/697 |
| 4,373,527 | 2/1983 | Fischell | 128/260 |
| 4,543,955 | 10/1985 | Schroeppel | 128/635 |
| 4,658,830 | 4/1987 | Sarnoff | 128/696 |
| 4,796,641 | 1/1989 | Mills et al. | 128/748 |
| 5,042,497 | 8/1991 | Shapland | 128/696 |
| 5,113,869 * | 5/1992 | Nappholz et al. | 600/508 |
| 5,135,004 | 8/1992 | Adams et al. | 128/696 |
| 5,305,745 * | 4/1994 | Zacouto | 600/324 |
| 5,313,953 | 5/1994 | Yomtor etal. | 128/696 |
| 5,330,505 | 7/1994 | Cohen | 607/6 |
| 5,404,877 * | 4/1995 | Nolan et al. | 600/484 |
| 5,409,009 | 4/1995 | Olson | 128/661.08 |
| 5,417,717 | 5/1995 | Salo et al. | 607/18 |
| 5,496,351 | 3/1996 | Plicchi et al. | 607/17 |
| 5,531,768 * | 7/1996 | Alferness | 607/6 |
| 5,730,125 | 3/1998 | Prutchi et al. | 128/637 |
| 5,792,066 * | 8/1998 | Kwong | 600/517 |
| 5,800,498 | 9/1998 | Obino | 607/123 |
| 5,876,353 * | 3/1999 | Riff | 600/547 |
| 6,112,116 * | 8/2000 | Fischell et al. | 600/517 |

* cited by examiner

Primary Examiner—Kennedy Schaetzle

(57) ABSTRACT

Disclosed is a system for detecting a myocardial infarction (i.e., a heart attack) at the earliest possible time and promptly warning the patient that he should immediately seek medical care. Specifically, a first embodiment of the present invention has an implantable electronic system that can sense a change in the patient's electrogram that is indicative of a myocardial infarction. If a myocardial infarction is sensed, the device would then cause an implantable or externally located alarm means such as an audio sound to be actuated to warn the patient of his condition. The patient could then promptly seek medical care, for example, at a hospital emergency room. Having been trained to recognize such an alarm, most patient would neither fail to recognize such an indication of a myocardial infarction nor would they ignore such an alarm signal if it were to occur. Since an implantable heart pacemaker or defibrillator already has within its structure many of the elements required for the device to recognize a myocardial infarction, it would be expeditious to add a capability to these existing devices to detect a myocardial infarction and provide an implantable or external alarm means to inform the patient to take appropriate action.

39 Claims, 4 Drawing Sheets

IMPLANTABLE ELECTRONIC SYSTEM WITH ACUTE MYOCARDIAL INFARCTION DETECTION AND PATIENT WARNING CAPABILITIES

FIELD OF USE

This invention is in the field of devices implanted within a person for the purpose of automatically detecting the onset of myocardial infarction and promptly warning that person to immediately seek medical care.

BACKGROUND OF THE INVENTION

Heart disease is the leading cause of death in the United States. The most prevalent form of heart disease is myocardial infarction resulting from a thrombus that obstructs blood flow in one or more coronary arteries. The sooner thrombolytic medication such as tissue plasminogen activator or urokinase is placed into the patient's bloodstream after the occurrence of a myocardial infarction, the sooner an obstructive thrombus will be dissolved and some perfusion of the myocardium can occur. The damage to the myocardium is strongly dependent on the length of time that occurs prior to restoration of some blood flow to the heart muscle. However, at this time, no implantable system exists that provides for early and automatic detection of myocardial infarction and for warning the patient that a myocardial infarction is occurring.

There are many patients who have implanted heart pacemakers or automatic defibrillators. The purpose of the pacemaker is to provide a low energy electrical stimulation pulse that causes the heart to beat at a prescribed rate. The purpose of the defibrillator is to shock the heart back into sinus rhythm after ventricular fibrillation has been detected. However, no existing implantable pacemaker or defibrillator is able to detect a partial or complete blockage of a coronary artery because of a thrombus in that artery and warn the patient that this potentially fatal event is occurring.

SUMMARY OF THE INVENTION

The present invention is a system for detecting a myocardial infarction (i.e., a heart attack) at the earliest possible time and promptly warning the patient that he should immediately seek medical care. Specifically, a first embodiment of the present invention has an implantable electronic system that can sense a change in the patient's electrogram that is indicative of a myocardial infarction. If a myocardial infarction is sensed, the device would then cause an implantable or externally located alarm means such as an audio sound source or a subcutaneous electrical tickle to be actuated in order to warn the patient of his condition. The patient could then promptly seek medical care, for example, at a hospital emergency room. Having been trained to recognize such an alarm, most patient would neither fail to recognize such an indication of a myocardial infarction nor would they ignore such an alarm signal if it were to occur.

Since an implantable heart pacemaker or defibrillator already has within its structure many of the elements required for the device to recognize a myocardial infarction, it would be expeditious to add a capability to these existing devices to detect a myocardial infarction and provide an alarm means to inform the patient to take appropriate action. Specifically, since an implantable pacemaker or defibrillator already has a long-lived battery and one or more electrodes connected by a lead wire to an electrogram amplifier within a hermetically sealed metal case. These same elements can be used for an implantable system to detect a myocardial infarction and alarm the patient accordingly.

It is well known that a myocardial infarction can be detected from a patient's ECG by noting an ST segment deviation (i.e., voltage change) as compared to the voltage of the patient's TP or PQ segments. Such an ST segment deviation can be even more clearly discerned with electrodes implanted within the body (especially within or in close proximity to the heart) as compared with detecting the elevated ST segment from chest and/or limb mounted electrodes. The electrical signal from the heart as measured from electrodes within the body is called an "electrogram". Thus the early detection of a thrombus causing myocardial ischemia is clearly feasible by using an implantable system that notes a change in a patient's electrogram. The implanted portion of such a system is defined herein as a "cardiosaver" device.

One embodiment of the present invention is a cardiosaver that can detect the occurrence of a myocardial infarction, i.e., a heart attack, within less than a minute after it occurs and then automatically alarm the patient that this event is occurring. The patient's warning can come from an alarm means implanted in the patient's body and/or from an externally located alarm means that receives a radio message from the implanted portion of the system. The entire system including the implantable part (the cardiosaver) and the external equipment is defined herein as the "cardiosaver system".

The implanted alarm means within the cardiosaver can be either an acoustic alarm or a subcutaneous electrical tickle. Either of these implanted signals could be applied periodically, for example at 30 second intervals, after the detection of a heart attack. The external alarm means would be accomplished by means of a radio receiving system that causes an audio alarm to occur when a radio signal is received from the cardiosaver. The external audio alarm would inform the patient that a myocardial infarction has been detected by his implanted system. It would also inform him that he should promptly take some predetermined medication such as aspirin, and he should promptly proceed to an emergency medical facility. The external equipment could also be programmed to call a rescue service to send an ambulance to bring the patient to an emergency facility. Still further, the external system could send the patient's electrogram to the rescue service so that they could be ready to provide medical treatment and advice based on the electrogram data.

It is believed that this system could be extremely valuable because many patients who have early symptoms of a myocardial infarction such as indigestion or left arm pain or even a chest discomfort very often tend to ignore these warning signs. If, for example, the patient experiences some indigestion that has an associated elevated ST segment that is indicative of a myocardial infarction, then promptly notifying the patient of this condition can significantly decrease the mortality and morbidity associated with acute myocardial infarction. Furthermore, as many as 20% of all patients who have a myocardial infarction have no detectable symptoms whatsoever. This is very often the case for elderly individuals who have had diabetes for many years. The invention described herein would be of particular value for such patients.

Thus it is an object of this invention to automatically sense that a myocardial infarction has occurred by means of an implantable device called a "cardiosaver".

Another object of this invention is to use the cardiosaver to warn the patient that a myocardial infarction has occurred by means of a subcutaneous electrical tickle or audio signal.

Still another object of this invention is to have an implantable myocardial infarction detection device (a cardiosaver) that sends a radio signal to a warning system that is located in close proximity to where the patient spends most of his time. That close proximity alarm system would inform the patient that he may be undergoing a myocardial infarction and that an ambulance has been called to bring him to a hospital and that he should take certain actions such as immediately going to an emergency room and/or promptly taking certain medications.

Still another object of this invention is to provide a means for informing the patient that he is having a myocardial infarction when he might otherwise ignore some particular symptom or he may not have had any detectable symptom.

Still another object of this invention is to provide a patient who has either an implanted heart pacemaker or defibrillator with the additional capability for sensing the occurrence of a myocardial infarction and promptly warning the patient that a myocardial infarction is occurring.

Still another object of this invention is to teach a method for informing diabetic patients who frequently have no symptoms associated with an acute myocardial infarction that they are having a heart attack and they should immediately seek medical assistance.

These and other objects and advantages of this invention will become obvious to a person of ordinary skill in this art upon reading of the detailed description of this invention including the associated drawings as presented herein.

DETAILED DESCRIPTION OF THE DRAWINGS

Figure 1:
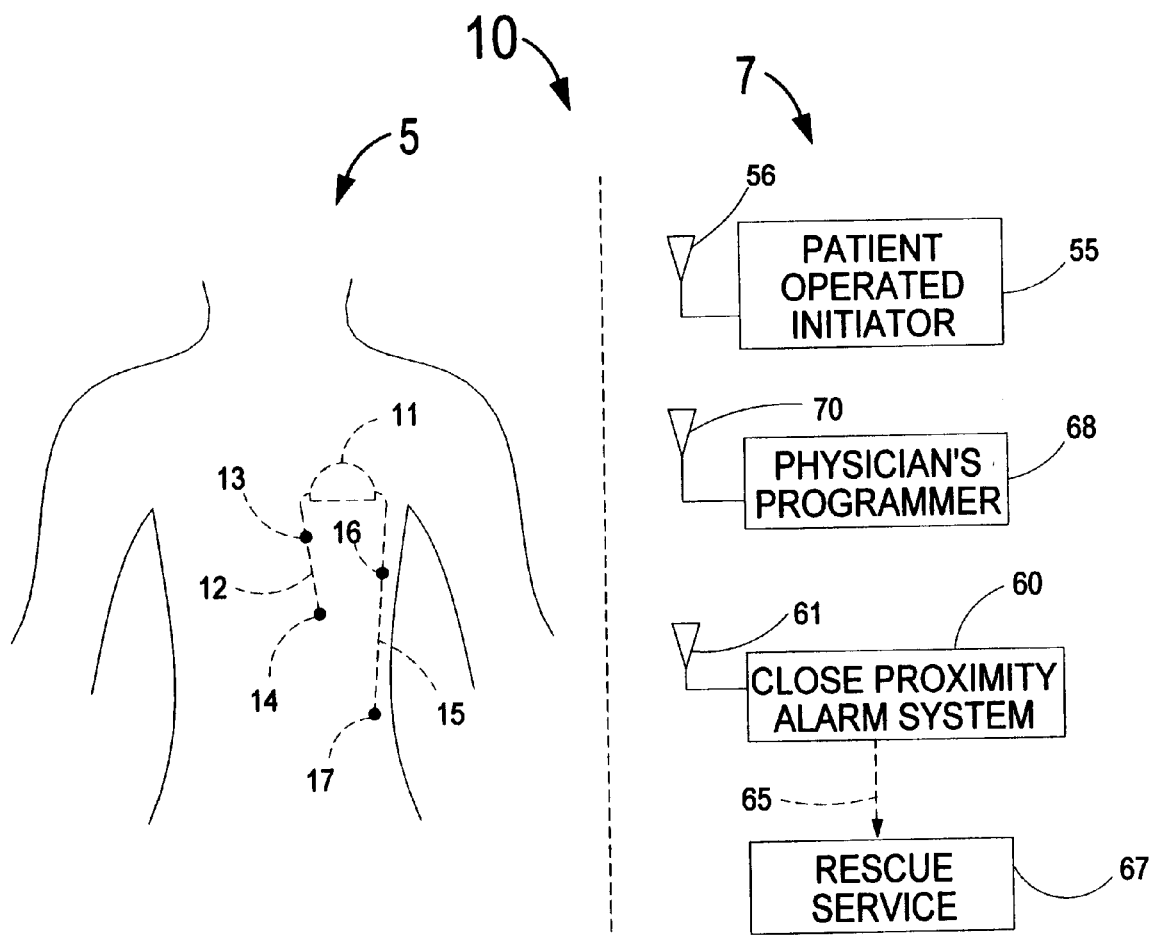
FIG. 1 illustrates a cardiosaver system for the detection of a myocardial infarction and for warning the patient that a myocardial infarction is occurring.

FIG. 1 illustrates the cardiosaver system 10 consisting of the implanted cardiosaver 5 and external support equipment 7. The cardiosaver 5 consists of an electronics module 11 that has two leads 12 and 15 that have multi-wire electrical conductors with surrounding insulation. The lead 12 is shown with two electrodes 13 and 14. The lead 15 has electrodes 16 and 17. In fact, the cardiosaver 5 could utilize as few as one lead or as many as three and each lead could have as few as one electrode or as many as four electrodes.

The lead 12 in FIG. 1 could advantageously be placed through the patient's vascular system with the electrode 14 being placed in the right ventricle close to the apex of the heart. The electrode 13 could be placed in the right atrium or the superior vena cava. The metal case of the electronics module 11 could serve as an indifferent electrode with either or both electrodes 13 and/or 14 being active electrodes. It is also conceived that the electrodes 13 and 14 could be used as bipolar electrodes. The placement and function of the lead 12 could be similar to that which is well known for leads used with heart pacemakers or defibrillators.

The lead 16 could advantageously be placed subcutaneously generally as shown in FIG. 1. Again for this lead 15, the case of the electronics module 11 could be an indifferent electrode and the electrodes 15 and/or 16 could be active electrodes or electrodes 16 and 17 could function as bipolar electrodes. The cardiosaver 5 could operate with only one lead and as few as one active electrode with the case of the electronics module 11 being an indifferent electrode.

The electronics module 11 contains a battery and electronic circuitry that can warn the patient when a myocardial infarction is occurring, can store for later read out the patient's electrogram, and can send radio signals to and receive radio signals from the external equipment 7. The functioning of the electronics module 11 will be explained in greater detail with the assistance of FIG. 6.

FIG. 1 also shows the external equipment 7 which consists of a patient operated initiator 55 having an antenna 56, a physician's programmer 68 having an antenna 70 and a close proximity alarm system 60 having an antenna 61 and a telephone line 65 that connects to a rescue service 67. The purpose of the patient operated initiator 55 is to give the patient the capability for holding in memory a particular electrogram that the patient wishes to have shown to his doctor. The purpose of the physician's programmer 68 is to change the operating parameters of the implantable cardiosaver 5 and to read out data stored in the memory of the electronics module 11 such as stored electrograms. The purpose of the close proximity alarm system 60 is to warn the patient when a myocardial infarction is detected by the cardiosaver 5 and to notify a rescue service 67 that an ambulance should be sent to bring the patient to a hospital emergency room. The functions of each portion of the external equipment 7 are explained in greater detail with the aid of FIG. 6.

Figure 2:
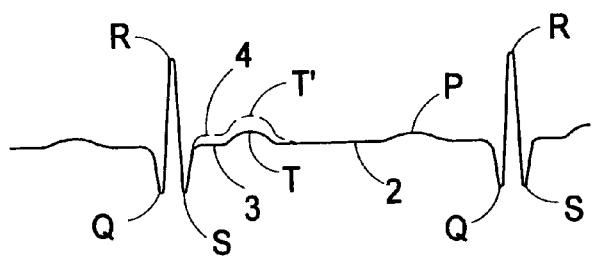
FIG. 2 illustrates a normal electrogram pattern and also shows an elevated ST segment that would be indicative of a myocardial infarction.
Figure 3:
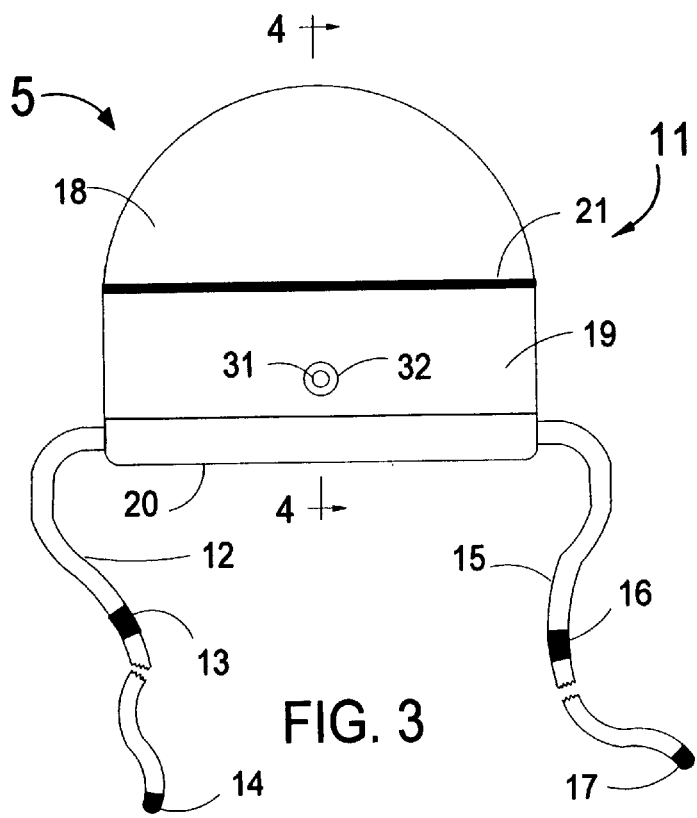
FIG. 3 is a plan view of the cardiosaver showing the cardiosaver electronics module and two electrical leads each having two electrodes.

FIG. 2 illustrates a typical electrogram signal from some pair of implanted electrodes such as the electrode 14 and the case 18 of FIG. 3. The various portions of the electrogram are shown as the Q, R, S, T and P waves. These are all shown as portions of a solid line in FIG. 2. The normal ST segment 3 is also shown in FIG. 2. When a myocardial infarction occurs, there is typically an elevation (or depression) of the ST segment 4 as shown by the dotted line in FIG. 2. It is this deviation of the ST segment 4 as compared to the undeviated segment 2 that is a clear indicator of a myocardial infarction. Although an elevated ST segment 4 can be a good indicator of a myocardial infarction, other indicators such as heart rate, heart wall motion or blood $pO_2$ could also be used as independent sensing means or those signals could be used in addition to the voltage deviation of the ST segment 4.

FIG. 3 is a plan view of the implanted cardiosaver 5 showing the electronics module 11, having a battery case 18, an electronics section case 19 and a header 20. Electrical conductors placed through the plastic header 20 connect the electronics module 11 to the electrical leads 12 and 15 which have respectively electrodes 13 and 14 and 16 and 17. The metal case 19 of the electronics section of the electronics module 11 is joined to the metal battery case 18 by a weld 21. On the metal case 19, a conducting disc 31 mounted onto an insulating disc 32 can be used to provide a subcutaneous electrical tickle to warn the patient that a myocardial infarction is occurring.

Figure 4:
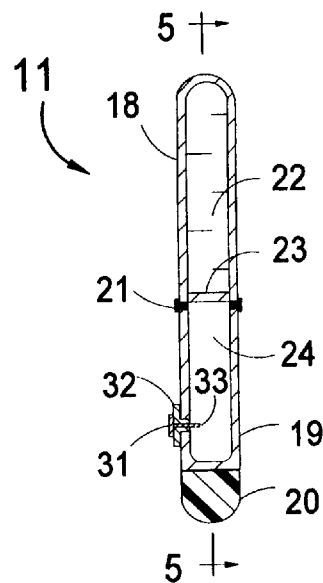
FIG. 4 is a cross section of the cardiosaver electronics module at section 4—4 of FIG. 3 showing separate sections for a battery, electronics and a header.

FIG. 4 is a cross section of the electronics module 11 at section 4—4 of FIG. 3. Shown in FIG. 4 is a battery 22 within a metal case 18 and having an end metal plate 23. A metal case 19 encloses an electronics section 24 that has a plastic header 20 within which electrical connections are made to the leads 12 and 15. Also shown in FIG. 4 is the cross section of the electrical tickle device consisting of the insulator disc 32 through which a wire 33 connects to the conducting disc 31. When an alternating voltage is applied between the conducting disc 31 and the metal case 19, the patient will experience a subcutaneous electrical tickle that can serve as a warning that a myocardial infarction has been detected. The weld 21 can be used to hermetically seal the battery case 18 to the case 19 of the electronics section 24.

Figure 5:
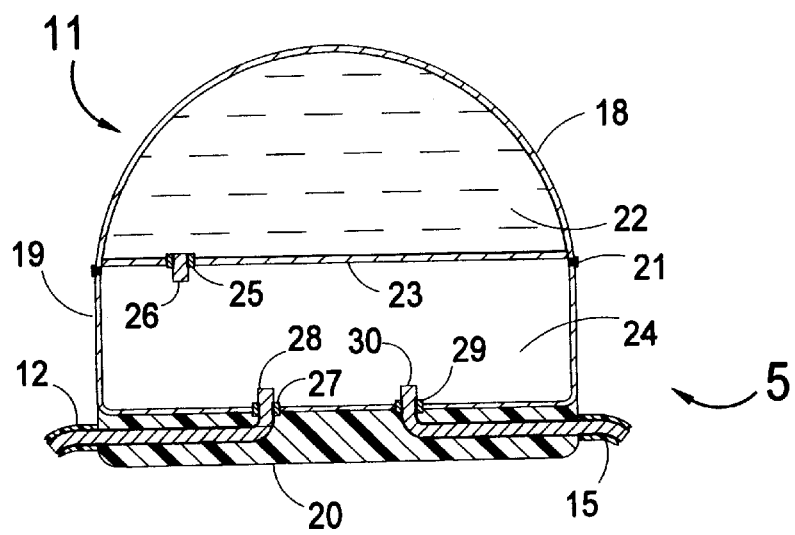
FIG. 5 is a cross section of the cardiosaver electronics module at section 5—5 of FIG. 4.

FIG. 5 is a cross section of the electronics module 11 at section 5—5 of FIG. 4. In FIG. 5 we see that the case 18 and the end metal plate 23 form a hermetically sealed enclosure for the battery 22. By this construction of having the battery case 18 formed as part of the case of the electronics module 11, a reduced thickness for the electronics module 11 can be accomplished. It is also envisioned that the battery 22 could be a separate device that is placed inside of a separate case of the electronics module 11.

FIG. 5 also shows a battery feed-thru 25 having a terminal 26 that is one terminal of the battery 22, the other terminal being the battery case 18. Going through the case 19 of the electronics module 24 are two feed-thrus 27 and 29 through which electrical connections are made respectively to the wire 28 of the lead 12 and the wire 30 of the lead 15. The feed-thrus 27 and 29 and the wires 28 and 30 are encapsulated in the plastic of the header 20. It should be understood that, if there are multiple electrodes in a lead, there must be more than one wire in that lead that passes through the header 20 and electrically connects to the electronics section 24.

Figure 6:
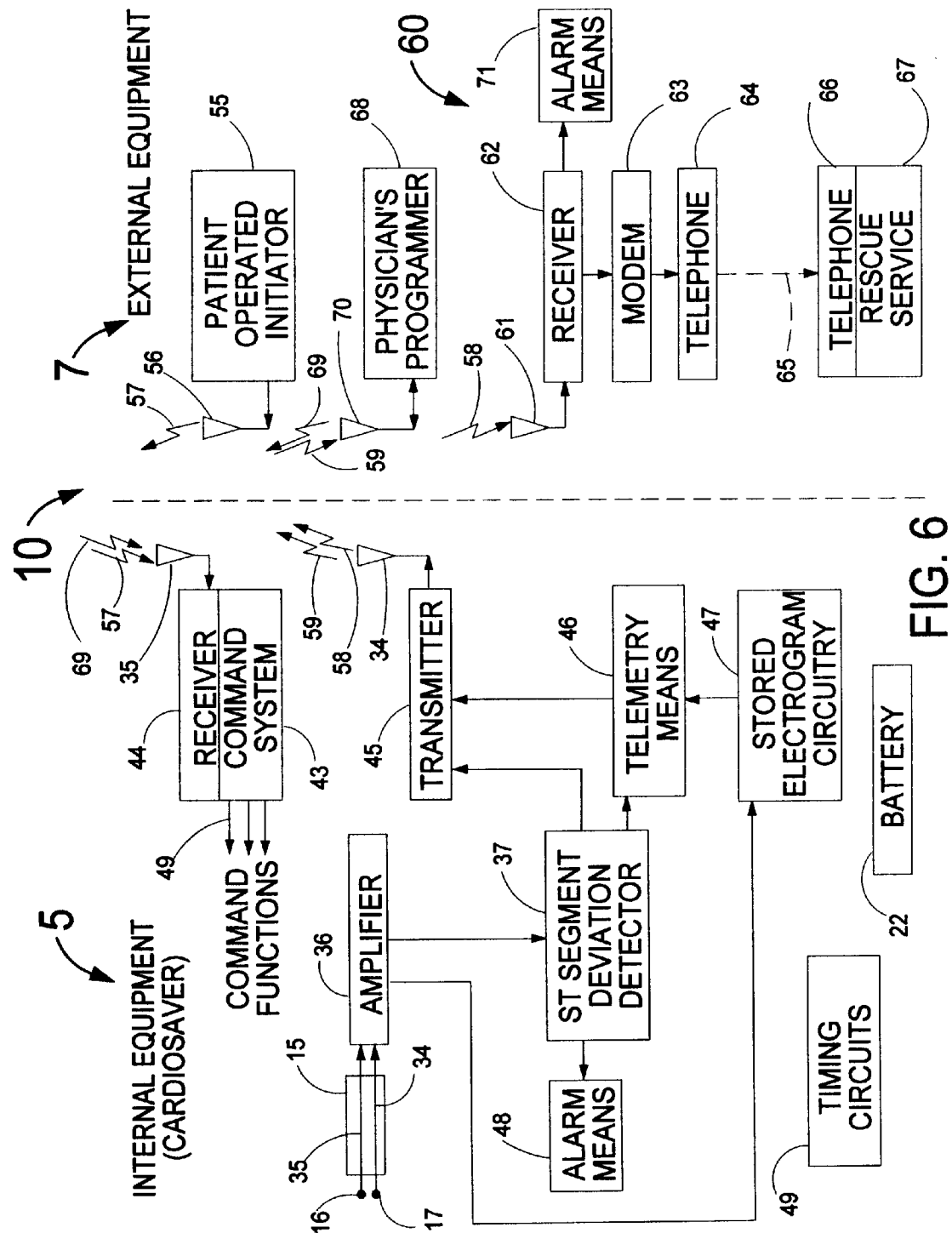
FIG. 6 is a block diagram of the cardiosaver system that illustrates the implantable and external portions of the system.

FIG. 6 illustrates in the form of a block diagram the entire cardiosaver system 10 consisting of the implanted cardiosaver 5 and the external equipment 7. The left side of FIG. 6 shows portions of the system that would be implanted in a patient who has a comparatively high probability for having a myocardial infarction. These would be patients who have already survived a first heart attack, or who have an implanted pacemaker or defibrillator or who have atherosclerotic disease or have had bypass surgery or who have a family history of heart disease. The right side of FIG. 6 illustrates equipment that would be situated externally to the patient.

FIG. 6 shows the electrodes 16 and 17 connected to an amplifier 36 by the wires 34 and 35 in the lead 15. The amplified electrogram signal from the amplifier 36 is fed into the ST segment deviation detector 37 and the stored electrogram circuitry 47. When an ST segment voltage deviation is detected by the ST segment deviation detector 37, an implantable alarm means 48 causes a subcutaneous electrical tickle or an audio warning signal to be produced that warns the patient that a myocardial infarction is occurring. Also, when an ST segment deviation is detected, the stored electrogram circuitry 47 holds a previous time period of electrogram recording in memory and then proceeds to record an additional time period of the patient's electrogram. The previous time period could be as short as 10 seconds or as long as 10 minutes. The additional time period could be as short as one minute or as long as 10 minutes.

When the ST segment deviation detector 37 detects a myocardial infarction, the transmitter 45 is turned on which causes a radio signal 58 to be transmitted out of the antenna 34 which is physically the wire 34 in the lead 15 or it could be a separate antenna. The signal 58 is then received by the antenna 61 of the receiver 62 of the external equipment 7. One output from the receiver 62 causes the alarm means 71 to emit an audio alarm to warn the patient that a myocardial infarction is occurring. The alarm means 71 could emit a loud ringing sound, or preferably a voice would inform the patient that: (1) his implanted equipment indicates that he may be having a heart attack; (2) he should take some previously agreed upon medication(s) such as aspirin or even be injected with an anti-thrombogenic agent such as heparin; (3) an emergency rescue service has been called; and (4) he should either immediately go to a hospital emergency room or he should wait for an ambulance to come with paramedics who are trained to treat heart attacks. Additionally, the alarm means 71 could include a flashing red light and/or written directions for the patient to follow. When a signal is received by the receiver 62 that a heart attack is occurring, a modem 63 would cause a telephone 64 to send a message over the telephone line 65 to the telephone 66 at a rescue service 67 which provides the rescue service 67 with the following information: (1) a specific patient is having a myocardial infarction, (2) the patient's name, address and a brief medical history, (3) a map and directions from the site of the rescue service to where the patient is located, and (4) the patient's stored and real time electrogram. If the rescue service is an emergency room at a hospital, information can be transmitted that the patient is in a car and on his way to the emergency room. In this manner the doctors at the emergency room could be prepared for the patient's arrival. The antenna 61, receiver 62, modem 63 and telephone 64 are collectively the close proximity alarm system 60 of FIG. 1.

The implanted alarm means 48 would typically be a sound or electrical tickle that had a duration of a few seconds and would be turned on approximately every 10 to 30 seconds for a time period of approximately 15 minutes. The physician's programmer 68 would have the capability of adjusting the intensity of the audio alarm and/or the intensity of the subcutaneous electrical tickle so that such an alarm is clearly discernible by the patient. The physician using the physician's programmer 68 could train each patient to recognize some clearly discernible audio or electrical tickle signal as an indication that the patient should immediately seek medical assistance. The physician's programmer 68 would also have the capability to enable or disable the implanted alarm means 48. The externally located alarm means 71 could remain on after it is activated by the cardiosaver 5 until it is manually turned off.

Returning now to a discussion of the cardiosaver system 10, an electrogram stored in the electrogram circuitry 47 of the implanted equipment 5 could be sent via the transmitter 45 by means of a radio signal 59 to both the physician's programmer 68 and receiver 62. The radio signal 59 arriving at the physician's programmer 68 would allow a physician to study the patient's electrogram and also receive other telemetry data such as battery voltage of the battery 22 inside the cardiosaver 5. Both the stored electrogram and real time electrogram could be sent by the radio signal 58 to the antenna 61 of the receiver 62. These data could then be transmitted to the rescue service 67 via the modem 63, the telephone 64, the telephone line 65 and the telephone 66. By studying the patient's stored and real time electrograms, paramedics or doctors at the rescue service could determine the patient's condition before the patient arrived at an emergency room.

The patient operated initiator 55 can be used by the patient to trigger some event such as holding in memory a particular portion of a recorded electrogram signal that the patient believes might be relevant to his medical condition. The patient operated initiator 55 would have an antenna 56 that would send a radio signal 57 to the receiver 44 of the command system 43 of the cardiosaver 5. Also the physician's programmer 68 can send a radio signal 69 out of its antenna 70 to the receiver 44 of the command system 43. These command signals could cause various command functions 49 to take place. For example, one command function 49 would be to change the threshold voltage level of the ST segment deviation detector 37 that would be recognized as a myocardial infarction. Other command functions 49 could be used to adjust the intensity of the audio alarm or subcutaneous tickle that warns the patient that a myocardial infarction is occurring. Still another set of command functions could adjust the time periods for the stored electrogram 47. For instance the time period for storing data prior to the detection of a myocardial infarction could be changed from 15 seconds to 60 seconds. This type of programming is well known in the art of heart pacemakers and implantable defibrillators.

The close proximity alarm system 60 would be placed where the patient would spend most of his time. Typically this would be at his home, although it could also be at another site such as a nursing home The distance from the cardiosaver 5 to the close proximity alarm system 60 should be less than 200 meters. It is also envisioned that the patient might carry on his body or in his clothing a repeater (specifically the transportable alarm means 77 of FIG. 7) that could receive a comparatively weak signal from the implanted cardiosaver 5 and relay that radio signal to the close proximity alarm system 60. The rescue service should be in reasonably close proximity to where the patient would spend most of his time.

If the start of a myocardial infarction is indicated, the patient could be aroused by the alarm means 71, even from sleep, to prepare for an ambulance to come to his home to take him to an emergency care facility. It is also conceivable that a companion or spouse of the myocardial infarction victim could take the patient to an emergency facility for treatment without waiting for the ambulance to arrive. If this were done, some simple means to inform the rescue service to not send an ambulance could be accomplished by telephone or by other means within the external equipment 7.

Returning now to other implanted equipment 5 shown in FIG. 6, the timing circuits 49 would provide all the timing signals required for the operation of the implanted equipment 5, and the battery 22 would provide the electrical power to operate all parts of the cardiosaver 5.

Figure 7:
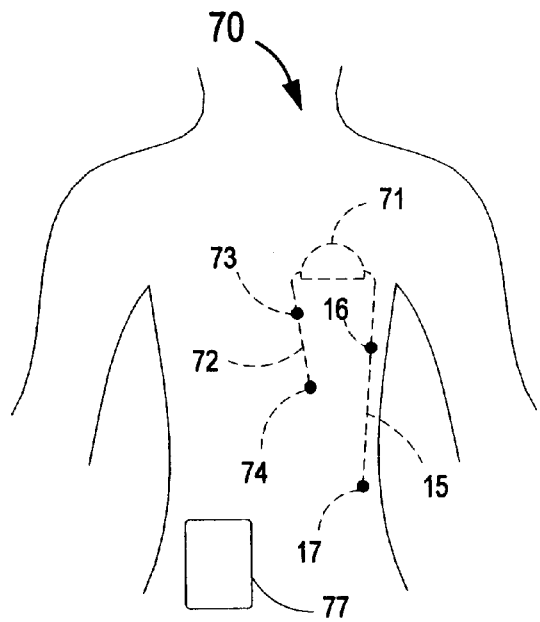
FIG. 7 illustrates an implantable system that includes a single device with cardiosaver plus pacemaker or defibrillator capability.
Figure 7:
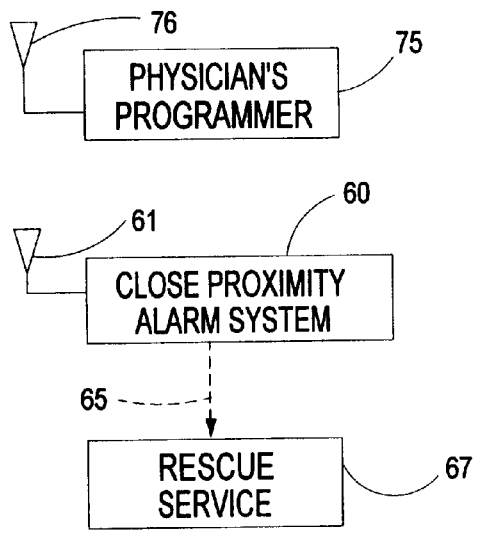

Although the cardiosaver system described herein could clearly operate as a stand alone system, it is clearly conceivable to utilize the cardiosaver system with a pacemaker or implanted defibrillator. The circuitry for the implanted portion of the cardiosaver system could also be included within the electronics section of such a pacemaker or defibrillator (as seen in FIG. 7). Furthermore, two separate devices (one pacemaker or one defibrillator plus one cardiosaver) could be implanted within the patient (as seen in FIG. 8).

FIG. 7 shows a pacer-cardiovertor-cardiosaver system consisting of an implanted pacer-cardiovertor-cardiosaver 70 and external associated equipment; the entire system being a pacer-cardiovertor-cardiosaver system. A pacer-cardiovertor is defined herein as the electronic circuitry for either a pacemaker or a defibrillator or the circuitry that can both pace or defibrillate a heart. The implanted pacer-cardiovertor-cardiosaver 70 consists of a single electronics module 71 that contains combined pacemaker and cardiosaver electronic circuitry or combined defibrillator and cardiosaver electronic circuitry. The lead 72 is placed in the patient's circulatory system; specifically, the electrode 74 is typically situated in the right ventricle near the apex of the heart, and an electrode 73 can be placed in the superior vena cava or in the right atrium. The electrode 74 could be an active electrode and a metal case of the electronics module 71 could serve as an indifferent electrode. The lead 72 with electrodes 73 and 74 could also be used for the cardiosaver portion of the electronics module 71. Alternatively, a separate lead 15 having electrodes 16 and 17 could be used by the cardiosaver portion of the electronics module 71 in exactly the same way as has been described for the cardiosaver system 10 of FIG. 1. Furthermore, the close proximity alarm system 60 including its antenna 61, telephone line 65 and rescue service 67 would also function as described for FIG. 1. However, the physician's programmer 75 of FIG. 7 having an antenna 76 would be used somewhat differently. The physician's programmer 75 differs from the physician's programmer 68 of FIG. 1 in that it would also have the capability for interacting with the pacer-cardiovertor portion as well as the cardiosaver portion of the electronic circuitry within the electronics module 71. Adding cardiosaver capability to existing pacemakers and/or defibrillators would make either of those devices more valuable in prolonging the life of a human subject in whom such a combined system is implanted.

FIG. 7 also shows a transportable alarm means 77 that can be worn or carried by the patient. Such a device would receive a radio signal from the implanted cardiosaver circuitry and it could respond in two different modes. One mode would be to immediately inform the patient by a comparatively loud human voice message that a myocardial infarction has been detected, he should take some medication and he should immediately proceed to an emergency medical facility. The other mode is to act as a relay device to cause the close proximity alarm system 60 to provide its audio message and also to call the rescue service 67. The advantage of the transportable alarm means 77 is that it can be with the patient wherever he might be. Also, being in very close proximity to the source of the radio signal from the implanted cardiosaver makes it easier to pick up the signal indicating that a myocardial infarction is occurring. The transportable alarm means 77 could be placed in the pocket of a man or in the pocketbook of a woman or it could be placed in a special vest-like device placed somewhere on the body of the patient.

Figure 8:
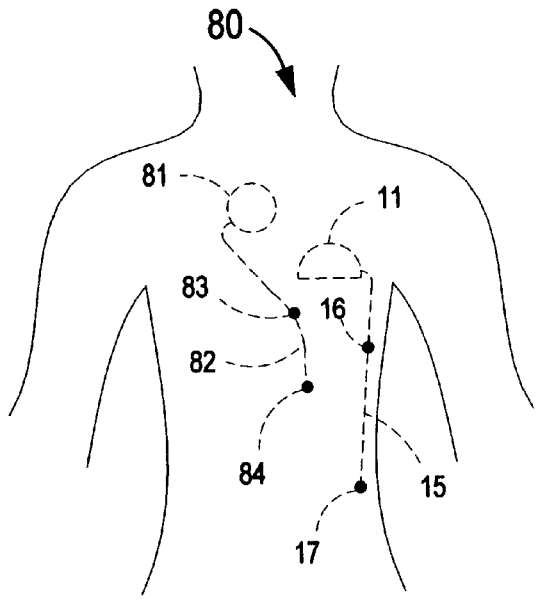
FIG. 8 illustrates two separate implantable devices which one of is a cardiosaver and the other is a pacemaker and/or a defiibrillator.
Figure 8:
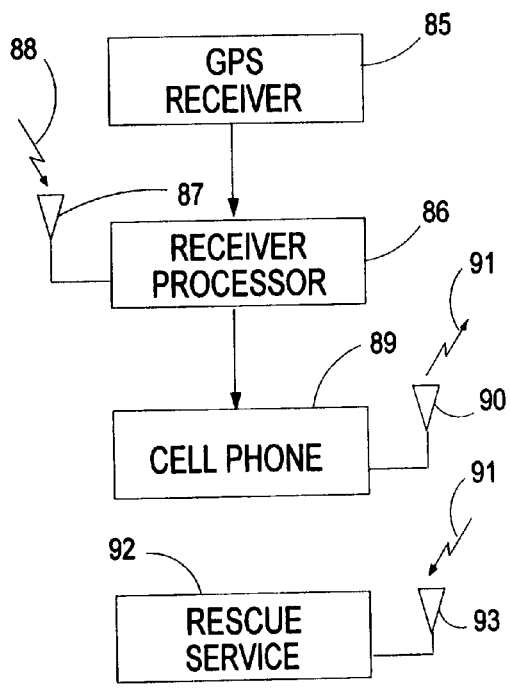

FIG. 8 is another alternative embodiment of the present invention that shows an implantable system 80 having a pacemaker or defibrillator electronics module 81 that is separate from a cardiosaver electronics module 11. The electronics module 81 has a lead 82 having electrodes 83 and 84 that, as previously described for electrodes 13 and 14 of FIG. 1 and 73 and 74 of FIG. 7, are situated within the patient's circulatory system. As before, the electronics module 11 having a lead 15 and electrodes 16 and 17 would be as described for FIG. 1. It is clearly feasible to implant both a pacemaker or defibrillator electronics module 81 and a cardiosaver 11 within a single human subject. The same external equipment as described for FIG. 7 could be used with the implanted system 80 of FIG. 8. However, an alternative embodiment for the external equipment is shown in FIG. 8. This equipment utilizes a GPS (satellite) receiver 85 as an input to the receiver processor 86 to provide a position identification for the patient at all times. This would be of value when the patient is away from his close proximity alarm system 60 of FIG. 1. When a signal indicating that the patient is having a heart attack is sent out from the implanted system 80, that radio signal 88 is received by the antenna 87 of the receiver processor 86. The receiver processor 86 then causes a cell phone 89 carried by the patient to send a radio signal 91 from the cell phone's antenna 90 to a receiving antenna 93 at a rescue service 92. In this way, all the attributes of the system as described for FIG. 1 can be accomplished even when the patient is away from his close proximity alarm system 60 of FIG. 1. Furthermore, this would be of particularly great value if the patient was both away from home and became unconscious when the myocardial infarction was occurring.

It is envisioned that the cardiosaver systems described herein would be of particular value to diabetic patients who are well known to have a myocardial infarction without any discernible symptoms. A method for helping such patients would be as follows:

(a) test the patient to determine if his fasting blood sugar exceeds 140 mg/dl, thereby indicating that he is a diabetic;

(b) determine if the patient is a likely candidate for a myocardial infarction because he has had either one, several or all of the following coronary problems: hypercholesterolemia a prior heart attack; atherosclerotic disease within his coronary arteries, bypass surgery or a family history of heart attacks;

(c) implant a cardiosaver within the patient, the cardiosaver having the capability for determining that a myocardial infarction is occurring and warning the patient that he should seek emergency medical assistance.

Such a method when used for diabetic patients could significantly reduce morbidity and mortality associated with acute myocardial infarction.

Although throughout this specification all patients have been referred to in the masculine gender, it is of course understood that patients could be male or female. Furthermore, although the only electrogram indication for a myocardial infarction that is discussed herein is a deviation of the ST segment, it should be understood that other changes in the electrogram (depending on where in the heart the occlusion has occurred and where the electrodes are placed) could also be used to determine that a myocardial infarction is occurring. Furthermore, sensors such as heart motion sensors, or devices to measure $pO_2$ or any other indication of a myocardial infarction could be used independently or in conjunction with a ST segment deviation detector.

Various other modifications, adaptations, and alternative designs are of course possible in light of the above teachings. Therefore, it should be understood at this time that within the scope of the appended claims the invention can be practiced otherwise than as specifically described herein.

What is claimed is:

1. A cardiosaver system for indicating to a human subject that a myocardial infarction is occurring, the system comprising:

an implantable sensor for detecting the occurrence of a myocardial infarction, the implantable sensor being adapted for implantation within the human subject, the sensor also having an output electrical signal that is the electrogram that is generated by the heart of the human subject;

an implanted alarm means for informing the human subject that a myocardial infarction is occurring, the implanted alarm means being adapted for implantation within the human subject;

the implantable sensor and the implanted alarm means both being parts of a cardiosaver that is adapted for implantation into the human subject; and the cardiosaver further comprising a radio transmitter that is adapted to transmit a radio signal to a close proximity alarm system which includes an external alarm means, the cardiosaver being adapted to simultaneously trigger the implanted alarm means within the human subject and activate the external alarm means within the close proximity alarm system when the cardsiosaver detects that the human subject is having a myocardial infarction.

2. The cardiosaver system of claim 1 wherein the implantable sensor is two or more electrodes.

3. The cardiosaver system of claim 2 wherein one of the electrodes is an active electrode and the cardiosaver further includes an implanted electronics module that has a metal case that acts as an indifferent electrode.

4. The cardiosaver system of claim 3 wherein the electronics module includes electronics circuitry that is adapted to detect the occurrence of a myocardial infarction from a deviation of the sensor's output electrical signal, the deviation being a change from the sensor's output signal when there is no myocardial infarction occurring.

5. The cardiosaver system of claim 4 wherein the'electronics circuitry within the electronics module includes a detector for detecting a ST segment deviation of the electrogram as an indication of myocardial infarction.

6. The cardiosaver system of claim 4 wherein the electronics circuitry within the electronics module includes means for recording the electrogram from the sensor, the means for recording the electrogram including a digital memory adapted to retain the electrogram for playback at a later time.

7. The cardiosaver system of claim 6 wherein the close proximity alarm system includes a telephone communication link that is adapted to automatically call an emergency medical services organization by means of the telephone link when the implanted cardiosaver detects the occurrence of a myocardial infarction in the human subject.

8. The cardiosaver system of claim 7 wherein the close proximity alarm system also includes means for receiving the electrogram as stored in the digital memory of the means for recording the electrogram of the implanted cardiosaver, the close proximity alarm system also including means for receiving the real time electrogram from the cardiosaver, the close proximity alarm system further including means for transmitting the stored electrogram and real time electrogram over the telephone link to the emergency medical facility.

9. The cardiosaver system of claim 1 wherein the implanted alarm means of the cardiosaver system further comprises means for producing a subcutaneous electrical tickle.

10. The cardiosaver system of claim 9 further comprising a physician's programmer located externally to the human subject, the physician's programmer including means for adjusting the intensity of the subcutaneous electrical tickle.

11. The cardiosaver system of claim 1 wherein the implanted alarm means of the cardiosaver system further comprises means for producing a sound that is an audio alarm that is an indication to the human subject that a myocardial infarction is occurring.

12. The cardiosaver system of claim 11 further comprising a physician's programmer located externally to the human subject, the physician's programmer including means for adjusting the intensity of the sound from the audio alarm.

13. The cardiosaver system of claim 1 wherein the close proximity alarm system includes memory storage means for storing a preset audio warning signal, the preset audio warning signal being produced by the close proximity alarm system when the implanted electronics module detects the occurrence of a myocardial infarction.

14. The cardiosaver system of claim 13 wherein the preset audio warning signal includes a description of at least one medication that is to be taken by the human subject.

15. The cardiosaver system of claim 13 wherein the preset audio warning signal includes instructions to proceed immediately to an emergency medical facility.

16. The cardiosaver system of claim 13 wherein the preset audio warning signal includes the statement that an ambulance is on its way to bring the patient to an emergency medical facility.

17. The cardiosaver system of claim 1 further comprising a radio receiver and command system as part of the implanted cardiosaver and a physician's programmer located externally from the human subject, the physician's programmer being adapted to receive radio signals from the implanted cardiosaver and to provide programming signals to be received by the receiver and command system of the implanted cardiosaver.

18. The cardiosaver system of claim 17 wherein the physician's programmer is adapted to display both real time and stored electrogram data that is sent by the radio signal from the implanted electronics module.

19. The cardiosaver system of claim 17 wherein the physician's programmer is adapted to receive telemetry data from the implanted electronics module and visually display those data.

20. The cardiosaver system of claim 1 wherein the external alarm means is a transportable alarm means that is adapted to be carried by the human subject, the transportable alarm means including a radio receiver and an audio alarm means, the transportable alarm means also being adapted to receive the radio signal from the implanted cardiosaver thereby informing the human subject by means of the audio alarm means that a myocardial infarction is occurring.

21. The cardiosaver system of claim 20 wherein the audio alarm means of the transportable alarm means includes a preset recording of a human voice.

22. The cardiosaver system of claim 1 further comprising an implanted electronics module that is adapted to receive command programming instructions from an externally located physician's programmer.

23. The cardiosaver system of claim 1 further comprising a physician's programmer and the implanted cardiosaver being adapted to be programmed by the physician's programmer to a specific voltage threshold of the electrogram above which voltage the cardiosaver will cause the implanted alarm means and the external alarm means to be actuated thereby indicating to the human subject that a myocardial infarction has been detected.

24. A system adapted for implantation within a human subject for the treatment of disorders of the heart, the system comprising an implanted electronic device for detecting and treating disorders of the heart of the human subjects, the implanted electronic device being a combination of a heart pacemaker and a cardiosaver, the heart pacemaker having heart pacemaker electronics circuitry adapted for providing electrical pulses to pace the heart and the cardiosaver having cardiosaver electronics circuitry adapted for detecting the occurrence of a myocardial infarction, the cardiosaver also having alarm means for alarming the human subject when a myocardial infarction is occurring.

25. The implanted system of claim 24 wherein the heart pacemaker electronics circuitry and the cardiosaver electronics circuitry are both contained within a single case.

26. The implanted system of claim 24 wherein the heart pacemaker electronics circuitry is contained within a first case and the cardiosaver electronics circuitry is contained within a second case that is separate from the first case.

27. The implanted system of claim 24 wherein the alarm means is an implanted alarm means that is an audio alarm implanted within the human subject.

28. The implanted system of claim 24 wherein the alarm means is an implanted alarm means that is an electrical tickle device implanted within the human subject, the electrical tickle device being adapted to warn the human subject that a myocardial infarction is occurring by means of a subcutaneous electrical stimulation signal.

29. The implanted system of claim 24 further comprising an external alarm means that is operable within 200 meters of where the patient is positioned.

30. The implanted system of claim 24 further comprising an external alarm means that is transportable and adapted to be carried by the human subject.

31. A system adapted for implantation within a human subject for the treatment of disorders of the heart, the system comprising an implanted electronic device for detecting and treating disorders of the heart of the human subject, the implanted electronic device being a combination of an implantable automatic heart defibrillator and a cardiosaver, the heart defibrillator having heart defibrillator electronics circuitry adapted for automatically providing a defibrillation electrical pulse to the heart when ventricular fibrillation is detected by the defibrillator electronics circuitry and the cardiosaver having cardiosaver electronics circuitry adapted for detecting the occurrence of a myocardial infarction, the cardiosaver also having alarm means for alarming the human subject when a myocardial infarction is occurring.

32. The system of claim 31 further comprising a heart pacemaker having heart pacemaker electronics adapted for providing electrical pulses to pace the heart.

33. The implanted system of claim 31 wherein the implantable defibrillator electronics circuitry and the cardiosaver electronics circuitry are both contained within a single case.

34. The implanted system of claim 31 wherein the implantable defibrillator electronics circuitry is contained within a first case and the cardiosaver electronics circuitry is contained within a second case that is separate from the first case.

35. The implanted system of claim 31 wherein the alarm means is an implanted alarm means for providing an audio alarm from within the human subject when a myocardial infarction is detected by the cardiosaver.

36. The implanted system of claim 31 wherein the alarm means is an implanted alarm means that is an electrical tickle device adapted for implantation within the human subject, the electrical tickle device being adapted to warn the human subject that a myocardial infarction is occurring by means of a subcutaneous electrical stimulation signal.

37. The implanted system of claim 31 further comprising an external alarm means that is operable within 200 meters of where the patient is positioned.

38. The implanted system of claim 31 further comprising an external alarm means that is readily transportable and adapted to be carried by the human subject.

39. A method to inform certain human subjects that a myocardial infarction is occurring, the method comprising the following steps:

(a) test the human subject to determine if that subject has a fasting blood sugar that is greater than 140 mg/dl;

(b) determine if the human subject has any one or more of the following conditions: a prior heart attack, a family history of heart disease, atherosclerosis, previous coronary bypass surgery or hypercholesterolemia;

(c) if the fasting blood sugar is greater than 140 mg/dl, and at least one of the conditions listed in (b) above exists, then implant within the human subject a cardiosaver system that is adapted to detect the occurrence of a myocardial infarction using an implanted sensor and electronics module which together are adapted to trigger an alarm that informs the human subject that a myocardial infarction is occurring.

* * * * *